(12) United States Patent
Koltz

(10) Patent No.: US 10,245,042 B2
(45) Date of Patent: Apr. 2, 2019

(54) CHECK VALVE VENTED STERILIZABLE POWERED SURGICAL HANDPIECE

(75) Inventor: Michael L. Koltz, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 323 days.

(21) Appl. No.: 13/419,129

(22) Filed: Mar. 13, 2012

(65) Prior Publication Data

US 2013/0245615 A1    Sep. 19, 2013

(51) Int. Cl.
*A61B 17/00* (2006.01)
*A61B 17/16* (2006.01)
*A61B 17/32* (2006.01)
*A61L 2/07* (2006.01)
*A61B 90/00* (2016.01)

(52) U.S. Cl.
CPC ...... *A61B 17/1622* (2013.01); *A61B 17/1628* (2013.01); *A61L 2/07* (2013.01); *A61B 17/32002* (2013.01); *A61B 2090/0813* (2016.02)

(58) Field of Classification Search
None
See application file for complete search history.

(56) References Cited

U.S. PATENT DOCUMENTS

| | | | | |
|---|---|---|---|---|
| 1,963,543 A * | 6/1934 | Linde et al. | ................. | 236/20 R |
| 2,171,292 A * | 8/1939 | Pieper | ................ | A61C 17/0202 |
| | | | | 251/240 |
| 3,120,845 A * | 2/1964 | Horner | .......................... | 606/180 |
| 3,642,002 A * | 2/1972 | Otterstrom | ..................... | 606/177 |
| 3,657,818 A * | 4/1972 | Garnier | ..................... | A61C 1/18 |
| | | | | 433/131 |
| 3,852,697 A * | 12/1974 | Snider | ........................... | 337/348 |
| 4,050,528 A * | 9/1977 | Foltz | .................. | A61B 17/1628 |
| | | | | 173/170 |
| 4,091,880 A * | 5/1978 | Troutner et al. | .............. | 173/217 |
| 4,233,982 A * | 11/1980 | Bauer et al. | .................. | 604/256 |

(Continued)

FOREIGN PATENT DOCUMENTS

CN    1088149 A    6/1994
CN    2730399 Y    10/2005

(Continued)

OTHER PUBLICATIONS

Microchek, Check Valves, Dec. 26, 2007 (Obtained from web.archive.org for the link http://www.microchek.com/html/microchek_valve.html captured at Dec. 26, 2007).*

(Continued)

*Primary Examiner* — Carl H Layno
*Assistant Examiner* — Manolis Pahakis
(74) *Attorney, Agent, or Firm* — Dicke, Billig & Czaja, PLLC

(57) ABSTRACT

A steam-sterilizable powered surgical handpiece provided with a check valve for venting of an interior cavity of the handpiece. The check valve may be configured to vent steam, steam condensate or contaminants from the interior cavity during a steam sterilization cycle. The check valve may be configured to open when subjected to steam sterilization parameters to prevent gas, liquid or contaminants from potentially degrading interior components of the handpiece.

17 Claims, 5 Drawing Sheets

(56) References Cited

U.S. PATENT DOCUMENTS

| | | | | |
|---|---|---|---|---|
| 4,289,131 A * | 9/1981 | Mueller | A61B 17/1633 | 277/377 |
| 4,331,277 A * | 5/1982 | Green | | 227/19 |
| 4,441,563 A * | 4/1984 | Walton, II | A61B 17/162 | 173/167 |
| 4,545,369 A * | 10/1985 | Sato | A61B 1/121 | 600/133 |
| 4,583,531 A * | 4/1986 | Mattchen | A61C 17/028 | 601/161 |
| 4,728,876 A * | 3/1988 | Mongeon | A61B 17/1624 | 310/50 |
| 4,741,731 A | 5/1988 | Starck et al. | | |
| 4,848,338 A * | 7/1989 | De Satnick et al. | | 606/1 |
| 4,873,461 A * | 10/1989 | Brennan | A61B 17/1628 | 310/154.12 |
| 4,878,484 A * | 11/1989 | Miyagi | A61B 1/31 | 600/133 |
| 5,080,983 A * | 1/1992 | Alexon et al. | | 429/54 |
| 5,136,220 A * | 8/1992 | Philipp | H02P 6/24 | 318/362 |
| 5,207,697 A * | 5/1993 | Carusillo et al. | | 606/167 |
| 5,259,365 A * | 11/1993 | Nishikori | A61B 1/00039 | 5/600 |
| 5,275,607 A * | 1/1994 | Lo et al. | | 606/169 |
| 5,309,714 A * | 5/1994 | Putney | B25B 21/004 | 173/219 |
| 5,352,416 A * | 10/1994 | Wagner | | 422/108 |
| 5,458,603 A | 10/1995 | Futch, Sr. | | |
| 5,464,350 A * | 11/1995 | Bierbaum | | 433/84 |
| 5,499,969 A * | 3/1996 | Beuchat | A61M 1/0058 | 128/DIG. 12 |
| 5,553,675 A * | 9/1996 | Pitzen et al. | | 173/217 |
| 5,554,896 A * | 9/1996 | Hogan | A61C 1/0053 | 235/472.01 |
| 5,571,633 A * | 11/1996 | Hagiuda | | 429/100 |
| 5,599,184 A * | 2/1997 | Field | | 433/115 |
| 5,620,459 A * | 4/1997 | Lichtman | | 606/205 |
| 5,747,953 A * | 5/1998 | Philipp | | 318/139 |
| 5,792,165 A * | 8/1998 | Klieman et al. | | 606/170 |
| 5,792,573 A * | 8/1998 | Pitzen et al. | | 429/97 |
| 5,804,936 A * | 9/1998 | Brodsky | G05B 19/0428 | 318/400.17 |
| 5,871,493 A * | 2/1999 | Sjostrom | A61B 17/162 | 604/22 |
| 5,944,520 A * | 8/1999 | Ash | A61C 1/057 | 433/126 |
| 5,967,285 A * | 10/1999 | Mohan et al. | | 192/103 F |
| 6,037,724 A * | 3/2000 | Buss | A61B 17/1626 | 310/47 |
| 6,059,806 A * | 5/2000 | Hoegerle | | 606/180 |
| 6,126,670 A | 10/2000 | Walker et al. | | |
| 6,146,137 A * | 11/2000 | Vogel | | 433/132 |
| 6,220,368 B1 * | 4/2001 | Ark et al. | | 173/178 |
| 6,257,351 B1 * | 7/2001 | Ark et al. | | 173/178 |
| 6,500,169 B1 | 12/2002 | Deng | | |
| 6,635,067 B2 | 10/2003 | Norman | | |
| 6,887,244 B1 * | 5/2005 | Walker et al. | | 606/80 |
| RE40,681 E * | 3/2009 | Pitzen et al. | | 429/97 |
| 7,535,135 B2 * | 5/2009 | Kardeis et al. | | 310/68 D |
| RE40,848 E * | 7/2009 | Pitzen et al. | | 429/100 |
| 7,638,958 B2 * | 12/2009 | Philipp et al. | | 318/139 |
| 7,740,628 B2 * | 6/2010 | Hoegerle et al. | | 606/27 |
| 7,922,723 B2 * | 4/2011 | Michelson | | 606/83 |
| 8,029,510 B2 * | 10/2011 | Hoegerle | | 606/80 |
| 8,080,011 B2 * | 12/2011 | Harp | | 606/85 |
| 8,403,949 B2 * | 3/2013 | Palmer et al. | | 606/169 |
| 8,459,414 B2 * | 6/2013 | Dexter et al. | | 184/7.4 |
| 8,485,818 B2 * | 7/2013 | Boutoussov | A61C 1/0046 | 433/26 |
| 8,545,502 B2 * | 10/2013 | Harp | | 606/85 |
| 9,301,771 B2 * | 4/2016 | Auclair, Jr. | A61B 17/1622 | |
| 9,358,672 B2 * | 6/2016 | Gauthier | B25B 23/1425 | |
| 2005/0065402 A1 * | 3/2005 | Moriyama et al. | | 600/133 |
| 2007/0085496 A1 | 4/2007 | Philipp | A61B 17/151 | 318/139 |
| 2007/0112377 A1 * | 5/2007 | Schneiter | | 606/205 |
| 2008/0154183 A1 * | 6/2008 | Baker | A61M 1/0058 | 604/28 |
| 2009/0024145 A1 * | 1/2009 | Meade | A61B 17/0482 | 606/144 |
| 2009/0030428 A1 * | 1/2009 | Omori et al. | | 606/130 |
| 2009/0216191 A1 * | 8/2009 | Loeffel | A61B 17/8822 | 604/131 |
| 2009/0261536 A1 | 10/2009 | Beale et al. | | |
| 2009/0264887 A1 * | 10/2009 | Beale et al. | | 606/80 |
| 2009/0264893 A1 | 10/2009 | Beale et al. | | |
| 2009/0264940 A1 | 10/2009 | Beale et al. | | |
| 2009/0292305 A1 * | 11/2009 | Kahler et al. | | 606/176 |
| 2009/0299439 A1 * | 12/2009 | Mire | A61B 17/1626 | 607/60 |
| 2009/0326537 A1 * | 12/2009 | Anderson | | 606/80 |
| 2010/0102517 A1 * | 4/2010 | Kumar et al. | | 277/553 |
| 2011/0009699 A1 | 1/2011 | Slenker et al. | | |
| 2011/0064978 A1 * | 3/2011 | McGahan | A61B 17/7091 | 429/61 |
| 2011/0065997 A1 * | 3/2011 | Hamer | A61B 17/32002 | 600/159 |
| 2011/0196266 A1 * | 8/2011 | Siebrecht et al. | | 601/2 |
| 2011/0202023 A1 | 8/2011 | Stanton et al. | | |
| 2011/0245599 A1 | 10/2011 | Auclair, Jr. et al. | | |
| 2011/0245833 A1 * | 10/2011 | Anderson | | 606/80 |
| 2012/0016376 A1 * | 1/2012 | Adams | A61F 2/2436 | 606/108 |
| 2012/0274253 A1 * | 11/2012 | Fair | B25B 13/461 | 318/434 |
| 2014/0012263 A1 * | 1/2014 | Marzella | A61B 17/1624 | 606/80 |
| 2014/0309666 A1 * | 10/2014 | Shelton, IV | A61B 17/068 | 606/139 |

FOREIGN PATENT DOCUMENTS

| | | |
|---|---|---|
| DE | 20202724 U1 | 6/2002 |
| JP | 2001-70226 | 3/2001 |
| WO | 2006037542 A2 | 4/2006 |
| WO | 2006111173 A1 | 10/2006 |
| WO | 2007002180 A2 | 1/2007 |

OTHER PUBLICATIONS

Kepner Products Company, 2010 Technical Catalog, Hydraulic and Pneumatic In-line and Cartridge Insert Conrtol Valves for any fluid or gas, 2010.*

International Search Report for Application No. PCT/US2013/030556, dated Jun. 18, 2013, 3 pages.

* cited by examiner

| SN | VALVE | CYCLES | CENSOR |
|---|---|---|---|
| BT-30 | YES | 206 | CENSOR |
| BT-29 | YES | 162 | CENSOR |
| BT-28 | YES | 152 | 0 |
| BT-25 | NO | 81 | 0 |
| BT-24 | NO | 89 | 0 |
| BT-23 | NO | 57 | 0 |

CHECK VALVE VENTED STERILIZABLE POWERED SURGICAL HANDPIECE

BACKGROUND

The present disclosure relates to a powered handpiece for driving surgical tools. More particularly, it relates to a check valve vented sterilizable powered surgical handpiece.

Powered surgical handpieces are commonly used in many medical specialties to drive surgical tools for performing various diverse functions. Many handpieces are reusable and may be cleaned or reprocessed via various techniques such as manual or automated washing or steam sterilization. Steam sterilization often involves placing a handpiece in an autoclave whereby the handpiece is subjected to high pressure steam while manual or automated washing involves rinsing, soaking or spraying a device with water and may involve the use of detergents or disinfectants. Over time, handpiece performance can degrade and/or handpieces might ultimately fail due to repeated washing and/or steam sterilization cycles. Performance degradation and handpiece failure can be due to handpiece seals, intended to prevent ingress of steam or water, gradually deteriorating or becoming damaged or weakened thereby allowing gas or liquid, such as steam or steam condensate from the washing or sterilization process, to collect within the handpiece. Thus, the seals intended to prevent ingress of water or steam during a wash or sterilization cycle serve to prevent egress of condensate or other contaminants from the interior of the handpiece. Over time the water, steam, condensate or other contaminants may accelerate corrosion of the internal handpiece components and/or may accelerate electromigration of internal electronic components. Therefore, the need exists for a means to vent gas, liquid or other contaminants contained within a handpiece, particularly during a sterilization cycle.

SUMMARY

According to an embodiment of the present disclosure, a check valve is incorporated into a surgical handpiece or driver for venting steam, steam condensate or contaminants which have collected in the interior cavity of the handpiece. The check valve is configured to provide fluid communication between an interior cavity of the handpiece and ambient air. The check valve is further configured to assume an open state whereby an evacuative flow of air is allowed to travel through the check valve in a direction out of the interior cavity and a closed state whereby the check valve substantially seals the interior cavity from ambient air.

According to other embodiments, a check valve is incorporated into a powered surgical handpiece or driver and may be configured such that in an open state an interior cavity of the surgical driver is in fluid communication with a passageway of the check valve and is open to air external to a housing of the surgical driver. The check valve may comprise a check valve configured to assume the open state when subjected to sterilization conditions whereby an interior cavity pressure exceeds an external pressure acting on the housing of the surgical driver.

The details of one or more embodiments of the present disclosure are set forth in the accompanying drawings and the description below. Other features, objects, and advantages of the disclosure will be apparent from the description and drawings, and from the claims.

DETAILED DESCRIPTION

Aspects of the present disclosure generally provide sterilizable surgical handpieces with a check valve for venting water, steam, steam condensate or contaminants, from an interior cavity of the handpiece where the elements to be vented are the result of a sterilization or wash cycle. As will be described in further detail below, check valves according to some aspects of the present disclosure may be configured to close and thereby seal the interior cavity of a handpiece when an external pressure acting on the handpiece is greater than internal pressure of the handpiece, such condition being the primary means for steam or contaminants to enter the handpiece. Check valves may further be configured to open to allow gas and/or liquid (e.g., steam and/or steam condensate) and/or other contaminants to exit the handpiece when an internal handpiece pressure is greater than the external pressure acting on the handpiece. As will be appreciated, the inherent thermodynamic processes of steam sterilization cycles, such as contemplated for use with the surgical handpieces described herein, create favorable conditions for handpiece venting via a check valve.

Figure 1:
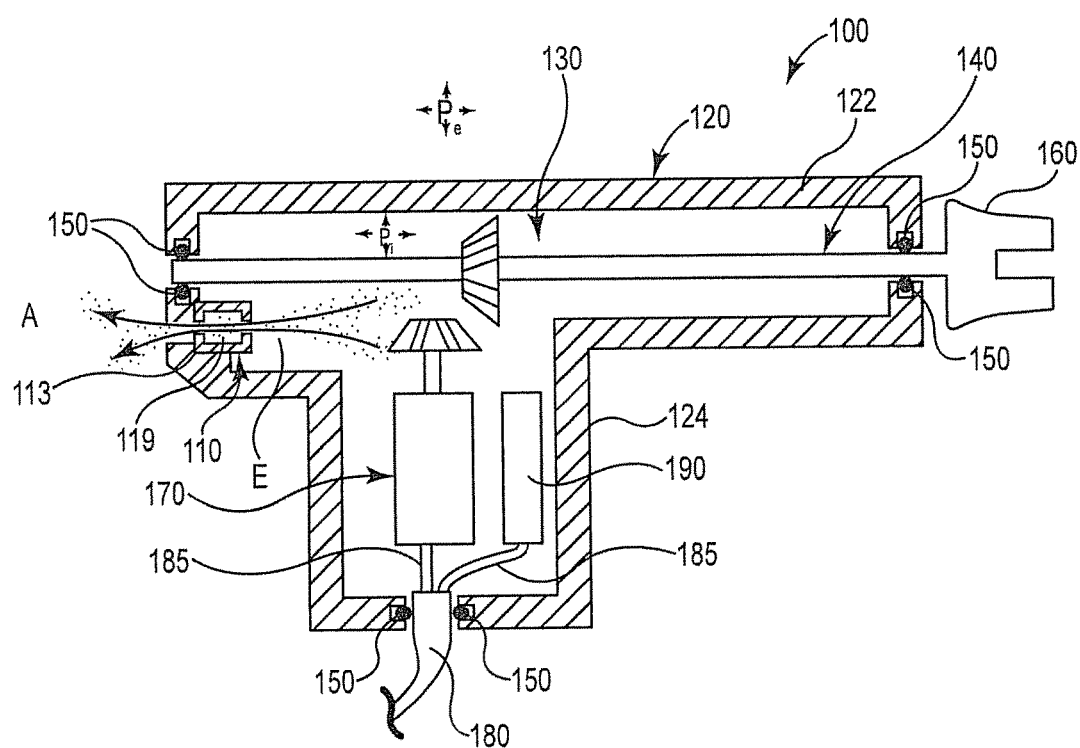
FIG. 1 depicts a cross-sectional illustration of a handpiece with a check valve in accordance with an embodiment.

FIG. 1 depicts a cross-sectional illustration of a surgical handpiece or driver 100 of the present disclosure. Surgical handpiece 100 includes housing 120 which defines a handle 124 and an interior cavity 130. The housing 120 may comprise materials known in the art as being sterilizable and/or autoclavable. Handpiece 100 includes a drive shaft 140 provided within housing 120. The drive shaft 140 extends through a portion of the housing wall 122 such that the drive shaft 140 extends to an exterior of the housing 120. Drive shaft 140 may be configured to drive a surgical tool (not shown). The drive shaft 140 may comprise an adapter 160 for coupling of a surgical tool (not shown) to the handpiece 100. Adapter 160 may be a quick-connect adapter 460 as described with reference to FIG. 4. Several non-limiting examples of surgical tools (not shown) useful with the handpiece of the present disclosure are cutting instruments, drilling instruments, taps, screw drivers, and set-screw break off instruments.

With continued reference to FIG. 1, surgical handpiece 100 comprises a motor assembly 170 and a printed circuit board (PCB) 190 disposed within the interior cavity. Electrical interconnects 185 couple the motor assembly 170 and/or PCB 190 to a power cable 180. Power cable 180 is provided through housing wall 124 and is configured to couple the motor assembly 170 and/or PCB 190 to an external power source (not shown) which may comprise an integrated power console (not shown). Alternatively, surgical handpiece 100 may comprise a battery (not shown) for powering handpiece 100. In this alternative battery-powered embodiment, handpiece 100 would not include power cable 180. One example of a battery-powered handpiece useful with the present disclosure is described in U.S. Patent Application Publication No. 20090264940 to Beale et. al., hereby incorporated by reference in its entirety.

As depicted in FIG. 1, handpiece 100 comprises seals 150 for sealing interior cavity 130 from ambient air A or from air external to housing 120. Seals 150 may include O-ring seals or any other seals as are known in the art. Seals 150 may be provided along housing 120, for example seals 150 may be disposed at locations where components (e.g., power cable 180, drive shaft 140) of handpiece 100 are provided through housing 120. By way of example, seals 150 may be provided at locations adjacent drive shaft 140 and/or power cable 180 for sealingly engaging shaft 140 and cable 180 with housing 120. In this manner, seals 150 serve to seal interior cavity 130 from matter (e.g., gas, liquid, contaminants) external to housing 120. Seals 150 may be placed at other various locations along or within housing 120 for sealing handpiece interior cavity 130 and to aid in protecting internal components of handpiece 100 such as motor assembly 170, PCB 190 and/or electrical interconnects 185 from matter such as gas, liquid or contaminants entering interior cavity 130 from outside of housing 120. Water, steam, steam condensate or other contaminants, such as generated during a wash or sterilization process as will be further elucidated in the ensuing discussion, can accelerate corrosion and/or electromigration of internal components. Thus, seals 150 may be provided to aid in protecting internal components (e.g., 170, 190 and the like) during a wash or sterilization process. Alternatively, components (e.g. 140, 170, 180) may be provided through housing in a press fit manner such that no seal or seals 150 are required.

Handpiece 100 further comprises a check valve 110. Check valve 110 may be provided at a location along or within housing 120 and may be integrated into housing 120 or may be a separate component disposed adjacent housing 120. It is to be understood that check valves 110, 210, 310, 410, 510 may comprise features described herein with specific reference to check valve 110 where like numerals represent like features. With reference to FIG. 1, check valve 110 includes a check valve housing or cartridge 113, a passageway 119 and a valve mechanism e.g., 115, 215, 315, 415, 515 as depicted in FIGS. 2A-D and FIG. 4A. A valve mechanism is not shown in check valve 110 of FIG. 1 for ease of illustration of the passageway 119 and evacuative flow of air E as described further herein below. Handpiece 100, 400 (FIG. 4A) and components of the handpiece including check valve 110, 510 (FIG. 4A) may comprise a variety of suitable materials including metals and metal alloys such as titanium, aluminum, magnesium, iron, cobalt, nickel, tungsten, steel or any combination thereof, and/or polymers including for example polyurethane materials, polyolefin materials, polyether materials, silicone materials or a combination thereof. Valve cartridge 113 may be sealed to housing 120 via a press fit which may include metal-to-polymer or metal-to-metal press fit or may include a slip fit with a seal such as seal 150 disposed circumferentially about cartridge 113. Check valve 110 is positioned or oriented within or along handpiece 100 such that when check valve 110 is in an open state, as depicted in FIG. 1, the interior cavity 130 is open to ambient air A and/or air external to housing 120. Conversely, when check valve 110 is in a closed or checked state (not shown in FIG. 1), check valve 110 substantially seals interior cavity 130 from ambient air and/or air external to housing 120. As illustrated in FIG. 1, interior cavity 130 is vented to ambient air A or air outside of housing 120 when check valve 110 is in an open state. With this configuration, an evacuative flow of air E is allowed to flow through passageway 119 of check valve 110 and out of interior cavity 130 to an exterior of housing 120. The evacuative flow of air E may comprise an array of contaminants and/or gas or liquid such as steam or steam condensate.

Figure 2A:
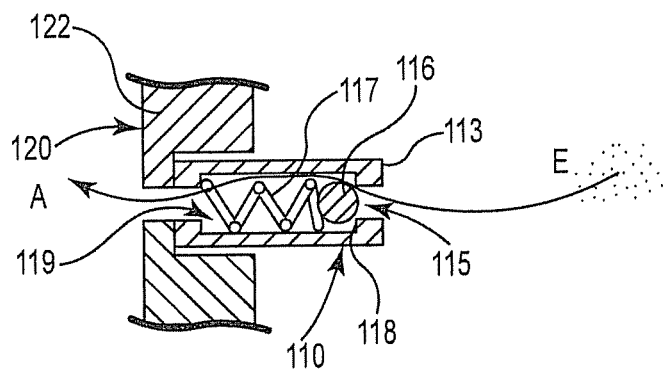
FIG. 2A depicts a cross-sectional illustration of a check valve for use with a handpiece in accordance with an embodiment.

FIGS. 2A-2D depict various check valves in accordance with the present disclosure. It is to be understood that check valve 110 may comprise any valve mechanism as is commonly known in the art and the valve mechanism is not limited to the examples depicted in FIGS. 2A-2D. For illustration, FIG. 2A depicts a check valve 110 including housing or cartridge 113. Check valve 110 is shown adjacent to a portion of wall 122 of housing 120 of the surgical handpiece 100 described with reference to FIG. 1. Check valve 110 is depicted as having a space between cartridge 113 and housing 120 however, check valve 110 may be press fit against housing 120 as described above such that essentially no open space exists between valve cartridge 113 and housing 120 in the area where check valve 110 abuts or is adjacent to housing 120. Check valve 110 comprises a valve mechanism 115 including a ball 116 and a spring 117. Valve mechanism 115 can be described generally as a ball check valve. Ball 116 may, in a checked or closed position (not shown) rest against a seat 118 of cartridge 113. Alternatively, seat 118 may include a seal (not shown) such as an O-ring or other seal as is commonly known in the art. When ball 116 is moved a distance from seat 118, as depicted in FIG. 2A, check valve 110 is in an open state whereby an evacuative flow of air E is allowed to exit an interior cavity 130 of a handpiece 100 (FIG. 1). The evacuative flow of air E is allowed to travel through passageway 119 of check valve 110 such that the evacuative flow of air E exits to ambient air A, or air outside of housing 120, for example E may exit to air in a sterilization chamber within which handpiece 100 has been placed, as will be described more fully herein below.

Figure 2B:
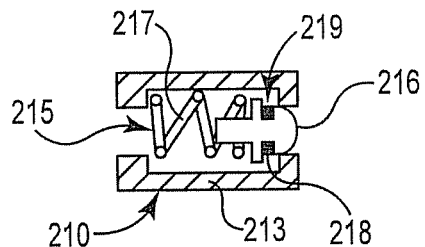
FIG. 2B depicts a cross-sectional illustration of a check valve for use with a handpiece in accordance with an embodiment.
Figure 2C:
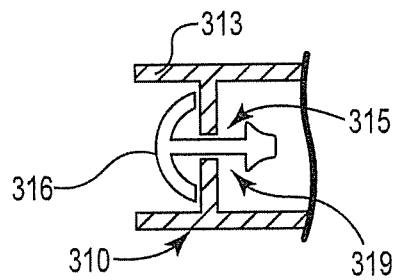
FIG. 2C depicts a cross-sectional illustration of a check valve for use with a handpiece in accordance with an embodiment.
Figure 2D:
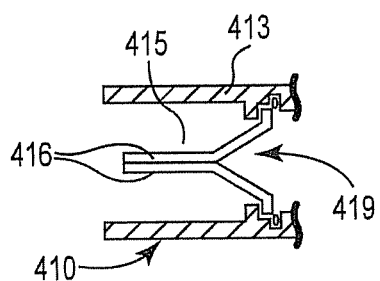
FIG. 2D depicts a cross-sectional illustration of a check valve for use with a handpiece in accordance with an embodiment.

Referring to FIGS. 2B-2D, examples of check valves according to the disclosure are shown apart from housing 120 of handpiece 100. FIG. 2B depicts an alternate embodiment of a check valve, namely check valve 210 including valve mechanism 215 comprising a poppet 216, an O-ring 218 and a spring 217. Check valve 210 is depicted in a closed or checked position thereby sealing a passageway 219. FIG. 2C depicts an alternate embodiment of a check valve 310 including valve mechanism 315 comprising an umbrella member 316. FIG. 2D depicts yet a further embodiment, check valve 410 which includes duckbill members 416. Check valves 110, 210, 310, 410 are shown for illustrative purposes are not intended to limit the structure of the types of check valves useful with the present disclosure.

Figure 3:
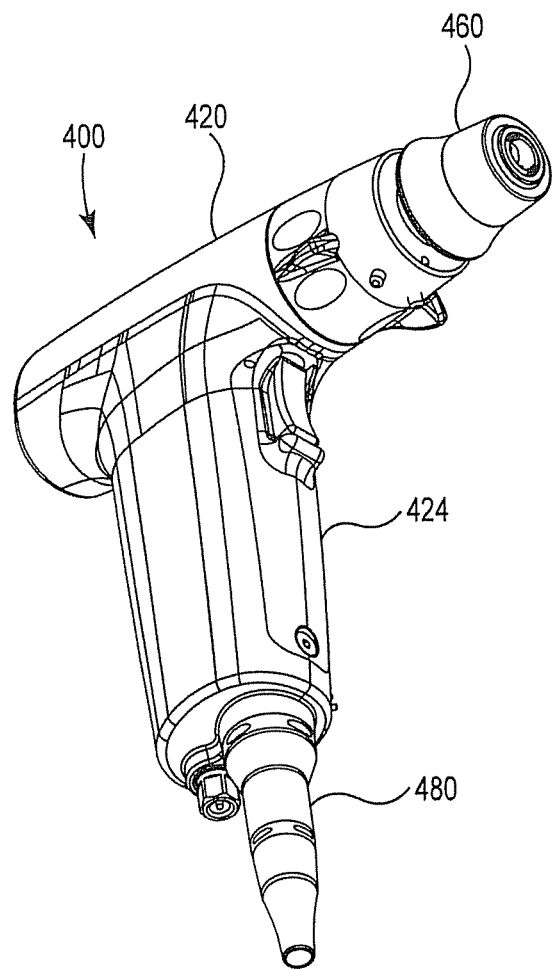
FIG. 3 is a perspective view of a powered surgical handpiece in accordance with an embodiment.

FIG. 3 depicts a perspective view of another embodiment of a surgical handpiece or driver according to the present disclosure. Handpiece 400 includes housing 420 defining a handle 424. An adapter 460 may be coupled to handpiece 400 and may be integral (i.e. non-removable) with handpiece 400. Quick-connect adapter 460 is configured to couple a surgical tool (not shown) to handpiece 400. One example of a quick-connect adapter 460 useful with handpieces 100, 400 is described in U.S. Patent Application Publication No. 20090261536 to Beale, et. al., hereby incorporated by reference in its entirety, while other configurations of a quick-connect adapter 460 are contemplated. With reference between FIGS. 3 and 4A, a power cable 480 extends from handle 424. The power cable 480 is configured to couple a motor assembly 470 to an external power source (not shown) which may comprise an integrated power console (not shown). Power cable 480 is provided through housing wall 420 and may include a cable seal member 483 disposed about a portion of power cable 480 for sealing power cable 480 with respect to housing 120.

Figure 4A:
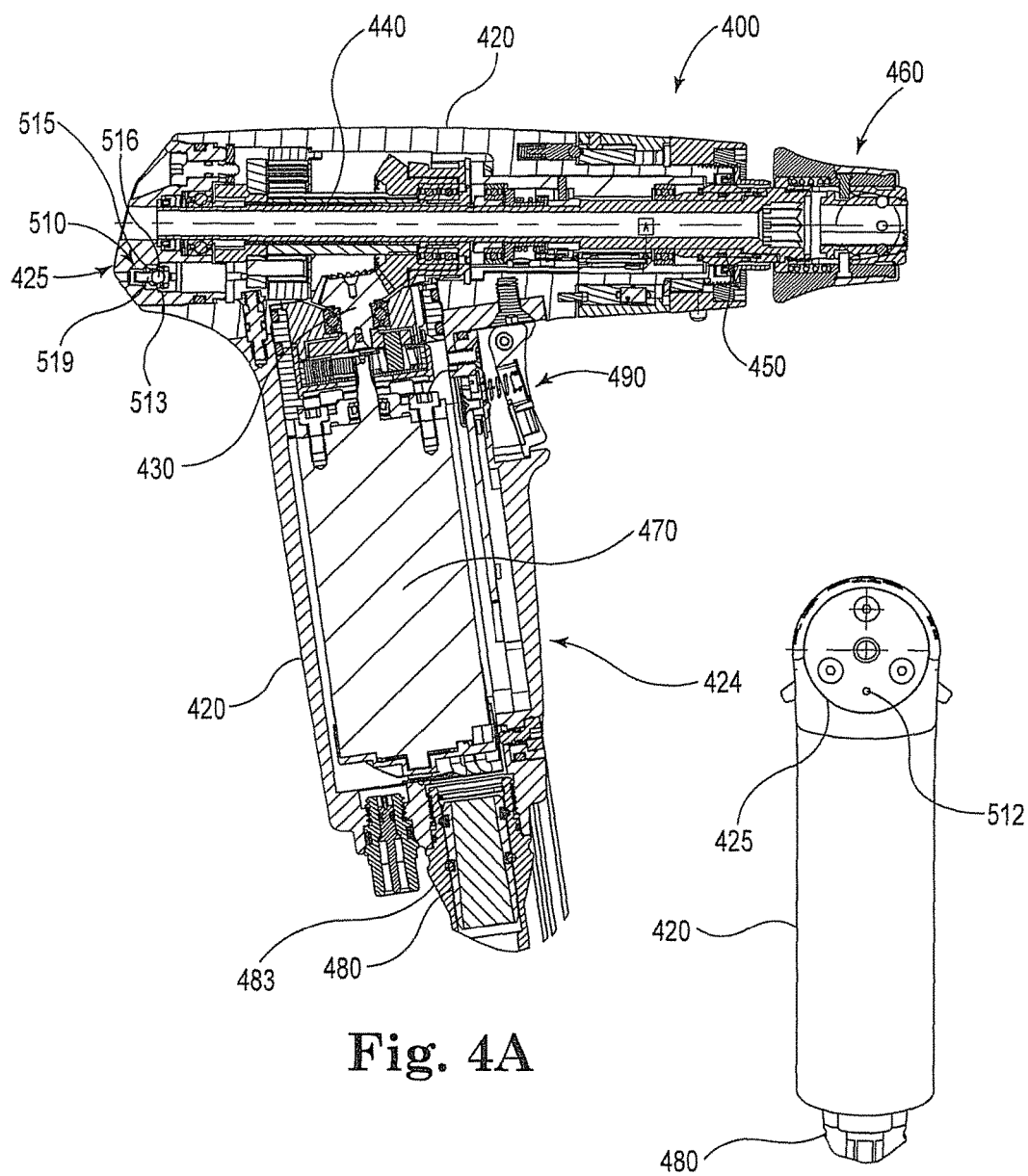
FIG. 4A is a cross-sectional view of the powered surgical handpiece of FIG. 3.

With specific reference to FIG. 4A, a cross-sectional view of the surgical handpiece of FIG. 3 is depicted. As with surgical handpiece or driver 100, surgical handpiece or driver 400 includes housing 420 defining a handpiece interior cavity 430 and a handle 424. A motor 470 is contained within handpiece 400 and specifically may be contained within the handle 424. A drive shaft 440 is disposed through the handpiece 400 and may extend to an exterior of housing 420. Trigger 490 is coupled to handle 424 and is configured to actuate motor assembly 470. Adapter 460, is coupled to drive shaft 440 and as described above is configured to couple a surgical tool (not shown) to handpiece 400. Some examples of surgical tools useful with handpieces 100, 400 are described in U.S. Patent Application Publication No. 20090264887 to Beale et. al. and U.S. Patent Application Publication No. 20090264893 to Beale et. al, hereby incorporated by reference in their respective entireties. Handpiece 400 may include a seal 450 or seals disposed adjacent drive shaft 440 and/or power cable 480 for sealing interior cavity 430 from ambient air A or air external to housing 120. Seal(s) 450 may be configured as described with reference to seals 150 of handpiece 100. For example, a seal 450 or seals 450 may be provided adjacent valve cartridge 513 described more fully herein below.

With continued reference to FIG. 4A, handpiece 400 includes a check valve 510 disposed at a location adjacent housing 420 and may be configured similar to check valve 110 described with reference to FIG. 1. Specifically check valve 510 comprises a check valve housing or cartridge 513, a passageway 519 and a valve mechanism 515 including a ball 516. Valve cartridge 513 comprises stainless steel and is sealed to housing 420 via a metal-to-polymer press fit, where endcap 425 described below comprises a polymer. Alternatively, cartridge 513 and housing 420 may be constructed of any other suitable metal, metal alloy or polymer as described above with reference to FIG. 1, such that cartridge 513 may be sealed to housing via a metal-to-metal press fit or a slip fit with a seal such as seal 450 disposed circumferentially about cartridge 513. Check valve 510 may be positioned or oriented within or along handpiece 400 such that when check valve 510 is in an open state, interior cavity 430 is open to ambient air A and/or air external to housing 420. Conversely, when check valve 510 is in a closed or checked state, check valve 510 may substantially seal interior cavity 430 from ambient air A and/or air external to housing 420. As described with reference to FIG. 1, interior cavity 430 is vented to ambient air A or air outside of housing 420, e.g. air within a sterilization chamber as described more fully herein below, when check valve 510 is in an open state. With this configuration, an evacuative flow of air E (not shown in FIG. 4) is allowed to flow through passageway 519 of check valve 510 and out of interior cavity 530 to an exterior of housing 420. The evacuative flow of air E may comprise an array of contaminants and/or may comprise gas or liquid such as steam or steam condensate.

Figure 4B:
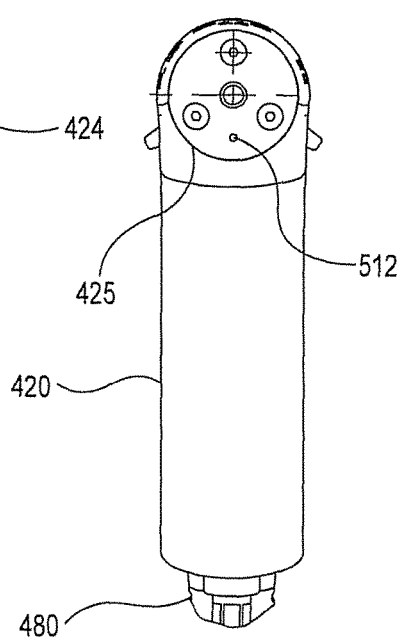
FIG. 4B is a posterior view of the powered surgical handpiece of FIG. 4.

FIG. 4B is a posterior view of the handpiece of FIG. 4A depicting an endcap 425. Endcap 425 may be provided in housing 420 to define a portion of handpiece housing 420 and includes channel 512 for receiving check valve cartridge 513 therein. Endcap 425 comprises a polymeric material specifically, a polyetheretherketone (PEEK), however endcap 425 may comprise a variety of other materials including metals and/or other suitable polymers as described herein above.

With reference to FIGS. 1 and 4A, surgical handpieces or drivers 100, 400 may be reusable or reprocessable devices. In many instances, reuse or reprocessing requires sterilization to ensure the device is adequately sterile for subsequent use in a surgical setting. Many sterilization techniques are known in the art, steam sterilization as but one example. Steam sterilization may involve placing a device to be sterilized in an autoclave chamber. Steam is then circulated within the autoclave chamber at a high pressure. The inherent thermodynamic processes of autoclave steam sterilization cycles create favorable conditions for handpiece (i.e. 100, 400) venting. For example, venting may occur during sterilization by two means. First, when a vacuum is generated in a pre-vacuum sterilization cycle and second when trapped condensate evaporates into steam during handpiece heating during all autoclave sterilization cycles.

Figures 5, 6:
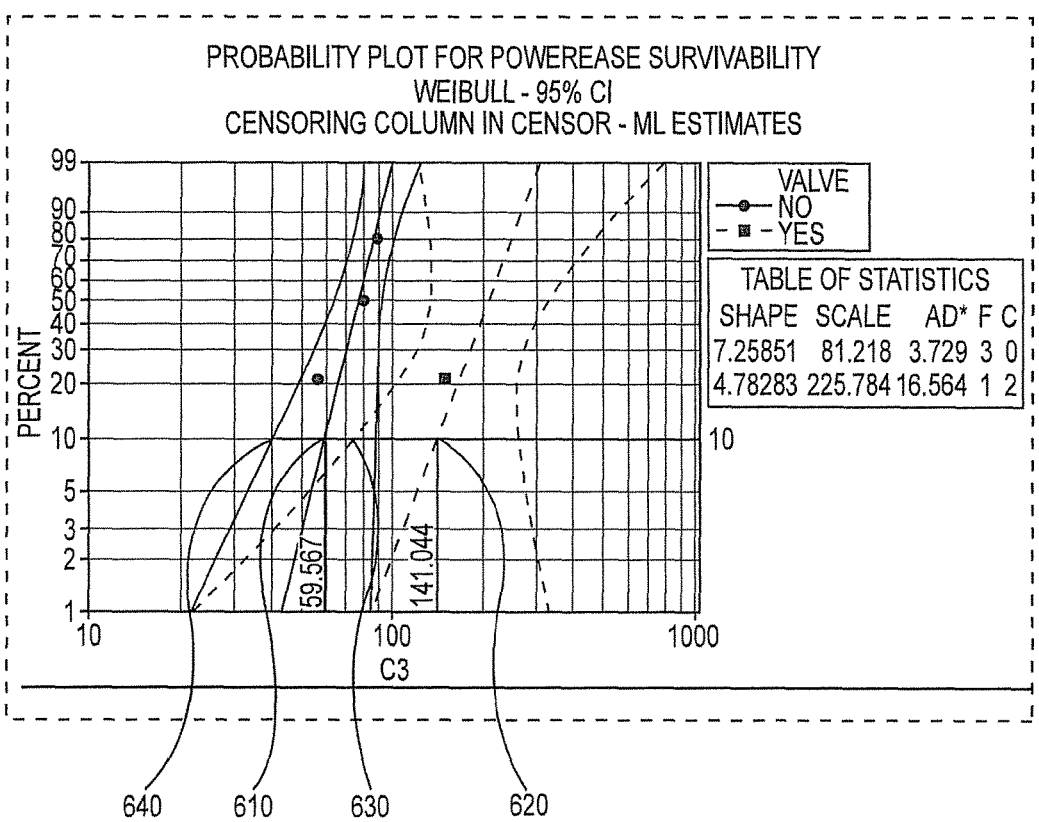
FIG. 5 is a table listing the number of sterilization cycles to failure for a sample of handpieces with check valves and a sample of handpieces without check valves.
FIG. 6 is a survivability plot depicting failure percentage vs. number of sterilization cycles for handpieces with check valves and handpieces without check valves.

A variety of surgical handpieces might benefit from check valve 110 described above and the specific configuration of handpiece 100 is not limited to the features described above. For example, handpiece 100 may be configured without handle 124 where motor 170 would be located in another portion of handpiece 100. In general, handpieces which might benefit from the check valve 110 of the present disclosure include handpieces including any of the following features in an internal cavity (e.g. 130): an electric motor not rated for steam sterilization, a printed circuit board, control electronics, an electrical sensor or sensors, Turning to FIGS. 5 and 6, testing was performed to evaluate the effects on handpiece reliability when adding a check valve to a surgical handpiece. FIG. 5 is a is a table listing the number of sterilization cycles to failure for a sample of handpieces 400 comprising check valves 510 (Check Valve sample) and a sample of handpieces 400 without check valves (No Check Valve sample). For the Check Valve sample, three surgical handpieces 400 were constructed substantially in accordance with the embodiment of FIG. 4A, with one exception being the absence of cable seal member 483 in the tested handpieces. Check Valve sample handpieces are listed in FIG. 5 as Serial Numbers (SN) BT-30, BT-29 and BT-28. For the No Check Valve sample, three surgical handpieces 400 were constructed identical to the surgical handpieces of the Check Valve sample with the exception of the check valve 510. No check valve was incorporated into the No Check Valve sample handpieces identified in FIG. 5 as Serial Numbers BT-25, BT-24 and BT-23.

Each of the Check Valve and No Check Valve sample handpieces were then subjected to a simulated use protocol which included a sequence of operations performed with each handpiece followed by a cleaning and a sterilization cycle. The sequence of operations included coupling of an appropriate surgical tool (e. g. a drill, a tap, a driver, a rod cutter, a post cutter or a set screw break off instrument) to the handpiece followed by performing the following operations with the handpiece upon a foam block: drill, tap, drive, rod cut, set screw break off, post cut. Each sequence of operations was followed by a manual or automated wash and an autoclave steam sterilization cycle of the handpiece only (i.e. the surgical tool was de-coupled from the handpiece prior to washing and sterilization). Manual cleaning included manually wiping all external surfaces of the motor and cable with a cloth dampened with an enzymatic detergent, brushing the motor, quick-connect and under the trigger area with a nylon brush dampened with detergent, and rinsing the handpiece under running water with the quick-connect end pointing down. The automated cleaning method included pre-washing the handpiece in cold tap water for two minutes followed by an automated wash cycle of five minutes at 66° C. using ENZOL® brand enzymatic detergent and finally rinsing the handpiece with hot tap water for one minute. The autoclave cycle included both autoclave with a drying cycle and autoclave without a drying cycle. For the autoclave cycles with drying, the handpiece was placed in an autoclave at 137° C. for 18 minutes. For the autoclave with a drying cycle, the handpiece was placed in an autoclave at 137° C. for 18 minutes followed by 42 minutes of drying time. For each handpiece, 75% of autoclave cycles did not include a drying time and 25% of drying cycles included a drying time. The CYCLES column of the table of FIG. 5 indicates the number of simulated use protocols (thereby the number of sterilization cycles) for each handpiece. Upon indication of a hard device failure, defined as a permanent degradation of an essential function of the handpiece to the point where alternate means of performing the surgical task (e.g. drilling, cutting, tapping, break off of set screw) were more efficient than continuing with the device, a handpiece underwent no further simulated use cycles. The number of simulated use (therefore sterilization) cycles for each device handpiece was recorded in the table of FIG. 5.

As depicted in the plot of FIG. 6, the number of sterilization cycles to failure for each sample of FIG. 5 was analyzed considering a 95% confidence interval. As can be seen from the plot, the Check Valve sample handpieces have a 90% reliability of 141 sterilization cycles to hard device failure (point estimate indicated at 620) while the No Check Valve sample handpieces are shown to have a 90% reliability of 60 sterilization cycles (point estimate indicated at 610). Thus, incorporating a check valve into a surgical handpiece such as disclosed herein, results in a remarkable 135% improvement in handpiece reliability. Even when considering the lower 90% reliability bound, Check Valve sample handpieces have a 90% reliability of 75 sterilization cycles to device failure (point estimate indicated at 630) versus 40 cycles for handpieces of the No Check Valve sample (point estimate indicated at 640). This represents an 88% improvement in handpiece reliability.

Although the present disclosure has been described with reference to preferred embodiments, workers skilled in the art will recognize that changes can be made in form and detail without departing from the spirit and scope of the present disclosure.

What is claimed is:
1. A surgical handpiece comprising:
a housing defining an interior cavity and defining a handle configured to be grasped by a user;
a motor assembly disposed within the handle, the motor assembly including a motor not rated for steam sterilization;
a drive shaft disposed through the housing;
an adapter coupled to the drive shaft and the housing, the adapter configured to couple a surgical tool to the handpiece; and
a check valve assembly including a check valve cartridge and a check valve, the check valve cartridge having walls extending into the interior cavity and defining a valve cavity, the check valve cartridge coupled to the housing and disposed internal to the housing, the check valve cartridge sealed to the housing via a press fit and including a seal disposed circumferentially about the check valve cartridge, the check valve disposed within the check valve cartridge, the check valve having an open state and a closed state, the check valve configured to provide fluid communication between the interior cavity and ambient air outside of the housing in the open state and prevent fluid communication between the interior cavity and ambient air outside of the housing in the closed state,
wherein the housing defines an open channel extending between the valve cavity and an exterior surface of the housing, and
wherein the housing, the motor assembly, the drive shaft adapter, and the sterilization check valve assembly are configured to be sterilizable and withstand steam sterilization in an assembled state of the surgical handpiece, and the sterilization check valve assembly is configured to be in an open state during steam sterilization.

2. The surgical handpiece of claim 1 wherein the check valve comprises a valve mechanism.

3. The surgical handpiece of claim 2 wherein the valve mechanism comprises at least one of the group consisting of:
a ball, a spring, an umbrella, a duckbill, a diaphragm, a swing, a tilting disc, a lift, and a stop-check mechanism.

4. The surgical handpiece of claim 3 wherein the check valve in the open state includes the interior cavity fluidly open to ambient air and an evacuative flow of air is permitted to travel through the check valve in a direction from the interior cavity to ambient air outside of the housing.

5. The surgical handpiece of claim 1 wherein the handpiece comprises a steam-sterilizable handpiece and further wherein the check valve is disposed adjacent the housing such that when subject to sterilization conditions, the check valve is configured to assume the open state to provide a vent for egress of a condensate from the interior cavity.

6. The surgical handpiece of claim 1 wherein the drive shaft extends from an exterior of the housing to the interior cavity, the drive shaft configured to supply a rotational force to the surgical tool.

7. The surgical handpiece of claim 1 wherein the surgical tool comprises one of:
a cutting member, a tap, a drill, a screw driver and a set screw break-off instrument.

8. The surgical handpiece of claim 1 wherein the adapter is a quick-connect adapter.

9. The surgical handpiece of claim 1 wherein the check valve cartridge is integral with the housing.

10. The surgical handpiece of claim 1 wherein the check valve is replaceable.

11. The surgical handpiece of claim 1 wherein the handpiece comprises a power cable configured to couple the motor assembly to an external power source.

12. The surgical handpiece of claim 1 wherein the handpiece comprises a battery-powered device.

13. A powered surgical driver comprising:
a housing comprising a housing wall, the housing wall defining an interior cavity and defining a handle;
a drive shaft disposed through the housing wall, the drive shaft configured to receive a surgical tool;
a motor assembly disposed in the housing, the motor assembly including a motor not rated for steam sterilization coupled to the drive shaft to provide rotational force thereto;
an end cap assembled to the housing wall, the end cap defining a channel fluidly open to air external to the housing and the end cap; and
a check valve assembly disposed within the channel and extending into the interior cavity, the check valve assembly comprising a check valve and a check valve housing including walls and defining a passageway fluidly coupled with the channel, the check valve configured to form a releasable seal at one of the walls of the check valve housing, the check valve housing sealed to the end cap via a press fit and including a seal disposed circumferentially about the check valve housing;
wherein the housing, the drive shaft, the motor assembly, the end cap, and the check valve assembly are configured to be sterilizable and withstand steam sterilization in an assembled state of the powered surgical driver, and
wherein the check valve is configured such that when the check valve is in the open state, the interior cavity is in fluid communication with the passageway and is open to air external to the housing during steam sterilization.

14. The powered surgical driver of claim 13 wherein the check valve is configured to assume the open state when subjected to an interior cavity pressure exceeding an exterior pressure.

15. The powered surgical driver of claim 14 wherein the check valve in the open state is configured to allow an evacuative flow of air comprising an array of contaminants to travel through the passageway in a direction out of the interior cavity.

16. The powered surgical driver of claim 14 wherein the check valve is configured to assume a closed state when the external pressure is greater than the interior cavity pressure.

17. The powered surgical driver of claim 13 further comprising at least one seal for sealingly engaging the drive shaft with the housing wall.

* * * * *